(12) United States Patent
Kvitrud et al.

(10) Patent No.: US 6,179,125 B1
(45) Date of Patent: *Jan. 30, 2001

(54) PACKAGED PHOTOCURABLE COMPOSITION

(75) Inventors: James R. Kvitrud, White Bear Lake; Thomas W. Martin, Little Canada, both of MN (US)

(73) Assignee: 3M Innovative Properties Company, St. Paul, MN (US)

( * ) Notice: Under 35 U.S.C. 154(b), the term of this patent shall be extended for 0 days.

This patent is subject to a terminal disclaimer.

(21) Appl. No.: 09/452,434

(22) Filed: Dec. 1, 1999

Related U.S. Application Data

(63) Continuation of application No. 09/122,677, filed on Jul. 27, 1998, now Pat. No. 5,996,796, which is a continuation-in-part of application No. 08/743,646, filed on Nov. 4, 1996, now Pat. No. 5,785,178.

(51) Int. Cl.[7] .............................. B65D 90/02; B65D 5/38; B55D 25/54
(52) U.S. Cl. .................. 206/459.1; 215/372; 220/665; 222/126
(58) Field of Search ............................. 206/459.1, 527, 206/63.5; 215/379, 365, 366; 220/663, 662, 665; 222/156, 207, 206, 51, 154, 215

(56) References Cited

U.S. PATENT DOCUMENTS

| | | |
|---|---|---|
| 1,085,560 | 1/1914 | Flynn . |
| 1,206,792 | 12/1916 | Aumuller . |
| 2,043,860 | 6/1936 | Morgan . |
| 2,293,475 | 8/1942 | Serra . |
| 2,294,473 | 9/1942 | Makeley . |
| 2,631,499 | 3/1953 | Riley . |
| 2,643,892 | 6/1953 | Riley . |
| 3,291,621 | 12/1966 | Hagedorn . |
| 3,655,985 | 4/1972 | Brown et al. . |
| 4,227,615 | 10/1980 | Flick . |
| 4,294,349 | 10/1981 | Ibsen et al. . |
| 4,785,953 | 11/1988 | Buchholz et al. . |
| 4,822,280 | 4/1989 | Rider . |
| 4,978,007 | 12/1990 | Jacobs et al. . |
| 5,100,320 | 3/1992 | Martin et al. . |
| 5,122,057 | 6/1992 | Discko et al. . |
| 5,172,809 | 12/1992 | Jacobs et al. . |
| 5,234,688 | 8/1993 | Gaffar . |
| 5,246,145 | 9/1993 | Leoncavallo et al. . |
| 5,328,058 | 7/1994 | Leoncavallo et al. . |
| 5,785,178 | 7/1998 | Kvitrud et al. . |
| 5,996,796 | 12/1999 | Kvitrud et al. . |

FOREIGN PATENT DOCUMENTS

| | | |
|---|---|---|
| 0114026 | 7/1984 | (EP) . |
| 237846 | 6/1925 | (GB) . |
| 1029537 | 11/1966 | (GB) . |

Primary Examiner—M. D. Patterson
Assistant Examiner—Anthony Stashick
(74) Attorney, Agent, or Firm—James D. Christoff

(57) ABSTRACT

A photocurable composition is provided which includes al having bottom and side walls which define a chamber a photocurable material disposed in-the chamber. The wall circulmacribe the bottom wall and includes a rant so that the side wall will substantially attenuate nic radiation while minimally attenuating visible light ng an approximating spectral wavelength greater than nanometers. By that arrangement, the level of the ocurable material may be visualized through the side while still providing sufficient attenuation of nic radiation to provide for long term storage of the ocurable material without substantial curing thereof.

10 Claims, 2 Drawing Sheets

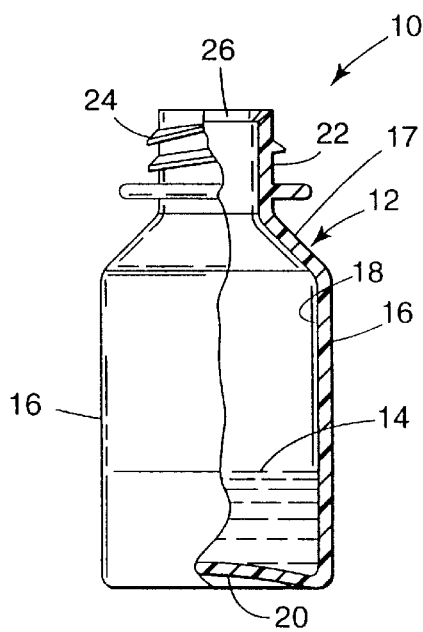
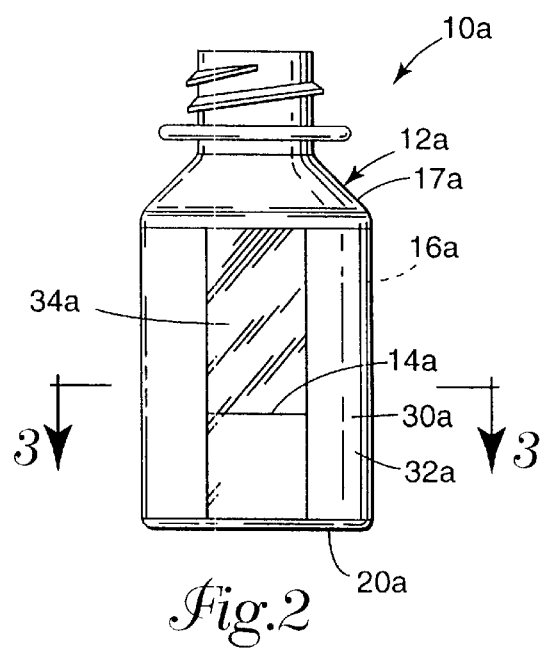
Fig.1
Fig.2
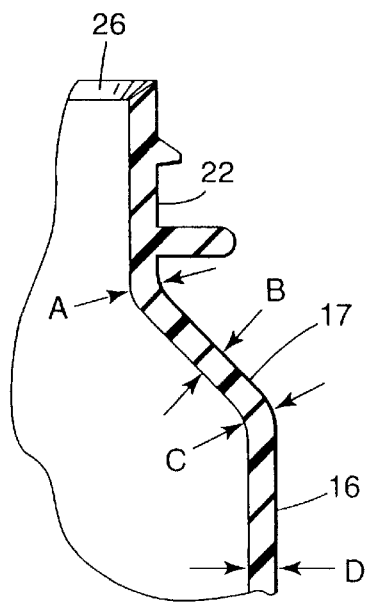
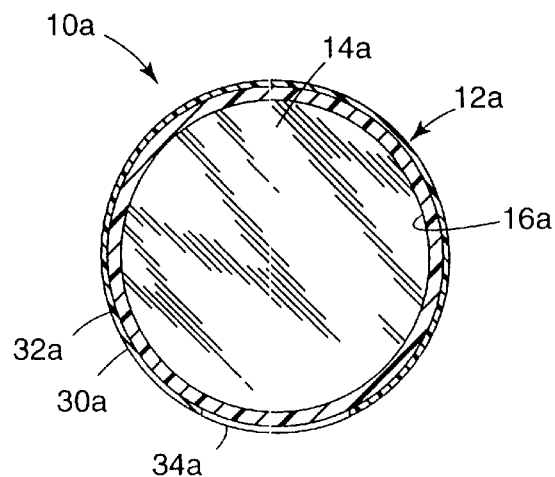
Fig.1A
Fig.3

PACKAGED PHOTOCURABLE COMPOSITION

CROSS-REFERENCED TO RELATED APPLICATIONS

This Patent Application is a continuation of application Ser. No. 09/122,677 filed Jul. 27, 1998, now U.S. Pat. No. 5,996,796 which is a continuation-in-part Application of an application entitled PACKAGED PHOTOCURABLE COMPOSITION, Ser. No. 08/743,646, filed Nov. 4, 1996, now U.S. Pat. No. 5,785,178.

BACKGROUND OF THE INVENTION

1. Field Of The Invention

This invention relates to a packaged photocurable composition that includes a squeezable vial having a chamber that receives a quantity of photocurable material.

2. Description of the Related Art

Many liquid and semi-liquid compositions used in small quantities in the household, commercial or industrial applications are sold in small vials, such as dropper bottles, squeezable applicators and the like. Typically, such vials are relatively inexpensive and are disposed of once their contents have been exhausted or have not been used by a specified expiration date.

Many small vials used for containing and dispensing liquid and semi-liquid compositions are made of a flexible polymeric material. To dispense the composition, opposed wall portions of the vial are squeezed together by finger pressure to expel the composition through an outlet. The flexible wall portions are an advantage in that the user can control, to some degree, the amount and flow rate of the composition that is dispensed. In addition, flexible wall portions are less likely to break if the vial is unintentionally dropped or subjected to other kinds of abuse in comparison to vials made of glass or other rigid materials.

Squeezable polymeric vials have been long used for various medical and dental preparations. Examples include vials for eye and ear medications, suntan and sun screen compositions, body lotions, cosmetics, topical ointments and insect repellents. Commercial and industrial applications include compositions for film developing and other photographic applications, adhesives (such as cyanoacrylates), lubricants and the like.

Many squeezable vials are made of polymeric material that is sufficiently transparent or translucent so that the user may visually estimate the amount of a composition remaining in the vial. In some instances, the transparent or translucent material helps the user ascertain whether or not the composition has degraded. For example, the user may be able to determine whether or not an adhesive has unduly hardened or thickened by shaking the vial and observing the fluidity of the contents through the polymeric wall portions.

Some compositions that are contained in squeezable vials are curable upon exposure to light having wavelengths in the visible spectrum. Examples of photocurable compositions include certain dental (including orthodontic) adhesives and primers, dental luting cements and other dental preparations such as sealants and crown build-up material. In the past, vials containing such photocurable compositions have included a sufficient amount of pigment, such as carbon black, that absorbs light and blocks substantially all of the light from entering the chamber in the vial that would otherwise unduly cure the contained composition.

Unfortunately, opaque squeezable containers are not entirely satisfactory, since the user cannot visibly ascertain, the amount of composition remaining in the vial or whether it has degraded. Some vials, and especially vials containing dental compositions, are relatively small and contain only a small amount of photocurable composition. With such vials, it is difficult to determine the amount of photocurable composition remaining therein by lifting the vial and estimating its weight, since the ratio of the weight of the vial to the weight of the composition is relatively large.

SUMMARY OF THE INVENTION

The disadvantages noted above with respect to conventional squeezable vials have been overcome by the present invention. In one aspect, the invention concerns a packaged composition that includes a vial formed by a bottom wall and an elastic side wall circumscribing the bottom wall to define a chamber. The side wall has an upper section shaped to form an outlet in open communication with the chamber. The bottom and side walls are formed of a polymeric material having a colorant added thereto for substantially attenuating actinic radiation and at least upright portion of the side wall is capable of transmitting light having wavelengths greater than 500 nanometers substantially uniform wall thickness. The packaged composition further includes a photocurable material disposed in the chamber that is cured responsive to exposure of actinic radiation. The photocurable material is dispensed through the outlet responsive to portions of the side wall being displaced from an initial position to a position closer together. The displaced portions of the side wall subsequently substantially return to the initial position.

Looking at the invention from another aspect, such concerns a packaged composition including a vial formed by a bottom wall and an elastic side wall circumscribing the bottom wall to define a chamber. The side wall has an upper section shaped to form an outlet in open communication with the chamber. The bottom and side walls are formed of a polymeric material having a colorant added thereto for substantially attenuating actinic radiation while minimally attenuating visible light having an approximating spectral wavelength greater than 500 nanometers through the side wall. The colorant has a color in the orange portion of the visible light spectrum. The side wall has a substantially uniform wall thickness. The packaged composition further includes a photocurable material disposed in the chamber and is cured responsive to exposure of actinic radiation. The photocurable material is dispensed through the outlet responsive to portions of the side wall being displaced from an initial position to a position closer together. Subsequently, the displaced portion of the side walls substantially return to their initial position. The packaged composition also includes a label secured to an external surface of a first portion of the side wall and extends from a position adjacent the bottom wall to a position adjacent the upper section thereof for enhancing visibility of a level of the photocurable material through a second portion of the side wall.

From still another aspect, the present invention concerns a packaged composition that includes a vial formed by a bottom wall and an elastic side wall circumscribing the bottom wall to define a chamber. The side wall has an upper portion shaped to form an outlet in open communication with the chamber. The bottom and side walls are formed of a polymeric material having a colorant added thereto for substantially attenuating actinic radiation, while minimally attenuating visible light having an approximating spectral wavelength greater than 500 nanometers through the side wall. The side wall has a substantially uniform wall thickness in an approximating range of 0.015–0.025 inches. The packaged composition further includes a photocurable material disposed in the chamber and being cured responsive to exposure of actinic radiation. The photocurable material is dispensed through the outlet responsive to portions of the side wall being displaced from an initial. position to a position closer together. Subsequently the displaced portions of the side wall substantially return to their initial position.

BRIEF DESCRIPTION OF THE DRAWINGS

FIG. 1 is a side elevation view of a packaged composition in accordance with one embodiment of the invention, and wherein a vial is cut-away in partial section in order to illustrate a quantity of the photocurable composition contained therein;

FIG. 1A is an enlarged sectional view of an upper portion of a vial side wall of the present invention;

FIG. 2 is a side elevation view of a packaged composition according to another embodiment of the invention;

FIG. 3 is a horizontal sectional view taken along line 3—3 of FIG. 2;

DETAILED DESCRIPTION OF THE PREFERRED EMBODIMENTS

Figure 4:
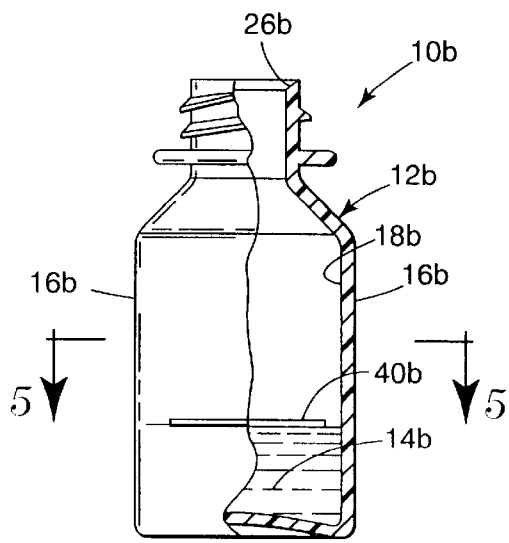
FIG. 4 is a side elevation view somewhat similar to FIG. 1 but in accordance with yet another embodiment of the invention.

A packaged photocurable composition according to one embodiment of the invention is illustrated in FIG. 1 and is designated by the numeral 10. The packaged photocurable composition 10 broadly includes a vial 12 and a photocurable material 14 therein.

The vial 12 includes a bottom wall 20 from which extends an elastic side wall 16 circumscribing the bottom wall to define a generally cylindrical internal chamber 18 therein. The photocurable material 14 is received within the internal chamber 18.

The side wall 16 has an upper section 17 shaped to form a neck portion 22 that terminates in an outlet 26. The neck portion 22 is provided with a threaded section 24 for coupling to a conventional threaded closure cap. The closure cap (not shown) has a dispensing opening and a closure for selectively covering that opening. A similar closure cap is described in U.S. Pat. No. 5,328,058, and such could be applied to the vial 12. Other types of dispensing outlets and closure caps may also be utilized.

The vial 12, including the elastic side wall 16 with its upper section 17, and the bottom wall 20 are preferably integrally molded and made of a polymeric material. The photocurable material 14 is dispensed from the vial 12 by displacing portions of the side wall 16 from an initial position, such as where opposing sides of the vial are substantially parallel, to a position where the sides are displaced so as to be closer together. The sides of the vial 12 are sufficiently elastic to substantially return to their initial position once the finger pressure of a user is released. Thus, in order for the vial 12 to be squeezable, the polymeric material from which it is formed should havp a flexural modulus that is preferably less than 200,000 kg/cm$^2$, and more preferably less than approximately 20,000 kg/cm$^2$, and most preferably less than 2,000 kg/cm$^2$. Referring additionally to FIG. 1A, the side wall 16 has a thickness D that is preferably in the range of approximately 0.005–0.1 inches (0.12–2.5 mm), and more preferably in the approximating range of 0.01–0.06 inches (0.25–1.5 mm). Most preferably, side wall 16 should have a thickness dimension D in the approximating. range of 0.010.03 inches (0.25–0.75 mm).

As will be discussed in following paragraphs, it is important that the wall thickness be substantially uniform throughout the side wall 16. Therefore, as the side wall transitions to the upper section 17, both the wall thickness C of the radiused portion 15 and the thickness B and A of the upper wall section 17 that transitions inwardly to form the outlet 26 should all be substantially equal to the thickness D. Thus, for a vial having a nominal thickness of 0.020 inches for the dimension D, the dimensions A, B and C should not vary more than ±0.005 inches in order to maintain a proper level of electromagnetic radiation absorption and transmissivity.

The flexural modulus and the thickness of the elastic side wall portions 16 are selected to enable opposed sections of the wall portion 16 to be readily squeezed together by finger pressure. As the opposed sections are squeezed together, free space in the chamber 18 is reduced and the photocurable material 14 in the chamber 18 is expelled through the outlet 26. The polymeric material from which the vial 12 is formed is sufficiently elastic to enable the squeezed sections thereof to fully self-recover from the deformed state to the original state of the vial, once the finger pressure is released, thereby re-assuming the normal, generally cylindrical configuration thereof.

As will be discussed in following paragraphs, another attribute of the polymeric material utilized for vial 12 is its transmissivity of visible light, allowing a user to ascertain the level of the photocurable material 14 disposed in chamber 18. Suitable polymeric materials for making the vial 12 include blow molded low density polyethylenes ("LDPE") such as No. 5104 from CHEVRON, high density polyethylene ("HDPE"), polyvinyl chloride ("PVC"), poly(ethylene glycol-co-cyclohexane-1,4-dimethanol terephthalate) ("PETG"), or poly(ethylene terephthalate) ("PET"). The selected polymeric material must also be compatible with the photocurable material 14 and not unduly degrade over an extended period of time.

The photocurable material 14 is a liquid or semi-liquid material that is curable upon exposure to selective actinic radiation, i.e., wavelengths of light (electromagnetic radiation) that effects curing in the material. Examples of photocurable material include dental (including orthodontic) adhesives and primers, luting cements, crown build-up material and sealants. Such materials have a photoinitiator (such as camphor quinone ("CPQ") ) that initiates curing when exposed to actinic radiation, which may be a portion of the electromagnetic spectrum having a wavelength less than 500 nm. The photocurable material 14 may also be a non-dental material such as a medical preparation or a composition intended for household, commercial or industrial application. The viscosity of the photocurable material must be within a range of values to be easily dispersed by squeezing portions of the side wall 16, and flow to the bottom of the chamber 18 without substantially coating the internal surface of the side wall, and thereby inhibiting visualization of the remaining portion of the photocurable material in the vial 12. Photocurable material 14 should have an absolute viscosity less than or equal to approximately 100 centipoise. With respect to kinematic viscosity, photocurable materials having viscosities within the approximating range of 120–1200 centistokes have been successfully utilized in the instant invention.

The vial 12 and in particular, the side wall 16 preferably transmits less than approximately 1.0% of actinic radiation, and more particularly, transmits less than approximately 0.5% of actinic radiation. Most preferably, less than approximately 0.2% of actinic radiation is transmitted through the side wall 16. As a result, the photocurable material 14 is able to remain in the chamber 18 for an extended period of time without unduly curing therein.

However, at least one upright portion of the side wall 16 must be capable of transmitting light having wavelengths greater than 500 nm, in order to transmit sufficient light in the visible spectrum to allow a user to see the photocurable material 14 therethrough, which photocurable material may be a transparent liquid. In that way, the level of the material 14 in chamber 18 can be determined.

As an example, if the photocurable material 14 is a dental adhesive that includes the photoinitiator that comprises CPQ, the adhesive will begin to cure when exposed to light having wavelengths approximating 470 n. Preferably, the wall material of the vial containing the dental adhesive blocks the passage of most of the light having such a wavelength, as well as light having wavelengths relatively close thereto. In such example, the wall portions preferably transmit less than approximately 1.0% of light having wavelengths in the range of 400 nm to about 500 nm.

In order to achieve the necessary wavelength sensitive transmittance, colorants such as pigments and/or dyes are useful for making the polymeric material absorb selective wavelengths of impinging electromagnetic radiation. The amount of colorant necessary per unit of polymeric material to provide the desired protection will vary depending on a number of factors, such as the particular colorant selected, the thickness of the wall sections of the vial, the uniformity of the wall sections of the vial, the wavelength of light to be absorbed and the capacity of the non-colorant treated polymeric material to absorb the light in the wavelengths to be filtered.

A suitable colorant for the dental adhesive vial mentioned above is a colorant having a manufacturer's identification No. 70344 HCP from TEKNOR COLOR COMPANY. The colorant is in the orange portion of the visible light portion of the electromagnetic spectrum. While colorants in the red portion of the spectrum have been found to suitably block actinic radiation, such as wavelengths less than 500 nm, they do not transmit sufficient visible light having wavelengths greater than 500 nm to allow a user to easily visualize the level of the photocurable material 14 within the vial 12. On the other hand, colorants within the yellow portion of the visible light spectrum transmit sufficient light having wavelengths greater than 500 nm, but do not sufficiently attenuate wavelengths less than 500 nm. It is a necessary requirement to substantially attenuate actinic radiation while minimally attenuating visible light having an approximating spectral wavelength greater than 500 nm, and colorants in the orange wavelengths have been found to meet that criteria.

The vial 12 may be made, for example, by mixing 6% by weight of the colorant with 94% of the LDPE "carrier" resin. The resultant mixture is then mixed with LDPE (such as No. 5104, from CHEVRON) at a "let-down" ratio of 5:1 (i.e., a ratio of five parts LDPE to one part carrier and colorant mixture by volume). More accurately, the overall mixture of colorant and resin should have a colorant concentration of approximately 1%. Preferably, the carrier resin has a slightly lower melting temperature than the melting temperature of the remaining quantity of LDPE, to facilitate mixing. A suitable carrier resin is yukalon Lm-30 from MITSUBISHI PETRO.

The amount of electromagnetic radiation attenuation is also dependent upon the thickness of the material through which the radiation passes. For vial 12, the side wall 16 has a thickness through which the electromagnetic radiation passes. The thicker the side wall 16 is, the greater the attenuation effect. However, as the vial 12 is intended to be a "squeeze bottle" the wall thickness cannot be so thick as to impede the displacement of opposing sides of the vial using only finger pressure. Thus, once a vial polymeric material and thickness has been selected, it then becomes critical that the wall thickness remain substantially uniform throughout the contours of the vial. As the upper section 17 of the side wall 16 is contoured to form the neck 22 of the vial and terminate in the outlet 26, there are several radiused bends in the cross-sectional contour of the vial. It is important that these radiused regions have substantially the same thickness as the unradiused portions thereof, in order not to attenuate less actinic radiation therethrough, or attenuate too much light in the wavelengths greater than 500 nm. Thus, the thickness of the vial radiuses A and C should be substantially equal to the wall thickness B and D. Similarly, the thickness of the side wall 16 where it interfaces with the bottom wall 20 should have a thickness which is not less than the minimum end of the side wall thickness tolerance.

A packaged composition 10a according to another embodiment of the invention is illustrated in FIGS. 2 and 3. The packaged composition 10a includes a vial 12a and a photocurable material 14a therein. Preferably, the vial 12a and the photocurable material 14a are the same or similar to the vial 12 and photocurable material 14 previously discussed, except for the differences noted in the paragraphs that follow. As a consequence, a detailed description of such previously discussed items will not be repeated.

As shown in FIGS. 2 and 3, the elastic side wall 16a of the vial 12a includes a label 30a that extends around the circumference of the vial 12a, and extends longitudinally along the length of the vial from a portion adjacent the bottom 20a to a position substantially adjacent the beginning of the upper section 17a of side wall 16a. The label 30a includes a first section 32a that is opaque or substantially opaque to the passage of light, especially light having wavelengths in the visible spectrum. The label 30a may also include a second section 34a that is transparent or translucent to light having wavelengths in the visible spectrum. Both of the sections 32a and 34a may be formulated to block the passage of all or at least a substantial portion of actinic radiation.

The label 30a may be made of any of a number of suitable materials, including polymeric film stock. Examples of suitable material include polyethylene labels from FLEX-CON COMPANY, INC. Optionally, the label 30a can be made of a co-extruded polyethylene film wherein the first section 32a is made of an extruded mixture of polyethylene and black, white or other pigment, while the second section 34a is simultaneously extruded from a stream of polyethylene without such pigment. As another alternative, the label 34a may be made of transparent or translucent polyethylene film and a quantity of ink applied to the first section 34a to render it opaque to the passage of light in the visible light spectrum. As a further option, the second section 34a is eliminated to define a gap between opposing edges of the label 30a, with the photocurable material 14a being viewed through the gap between opposing end portions of the label 30a. The window created between the opposing edges of the label 30a, or through the unpigmented section 34a of label 30a enhances the contrast between the photocurable material and the air space above the photocurable material in the internal chamber 18. As many of the photocurable materials which may be packaged in vial 12 are substantially transparent, it is important that a contrasting background be created for viewing the height of the photocurable material within the vial 12. For vials 12a of small size, it is currently not technically feasible to co-mold the vial itself with a single portion thereof having a substantially transparent or translucent portion and a remaining portion being substantially opaque to visible light. Therefore, for such vials of small size, it is critically important that the label produce a substantially opaque section which occupies more than 50% of the circumference of the vial for providing contrast to view the photocurable material through a remaining portion of the circumference of the vial, i.e. the portion 34a.

Although not shown in the drawings, one side of the label 30a is coated with a pressure-sensitive adhesive to firmly secure the label 30a to the upright side wall 16a. An example of a suitable adhesive is a 0.0008 inch (0.04 mm) thick layer of a permanent acrylic adhesive (No. V-157 from FLEXCON). Preferably, where the label 30a includes a transparent portion 34a, adjacent end sections of the label 30a overlap in order to reduce the likelihood of flagging and assure that the end portions of the label 30a tightly adhere to the side wall 16a.

As previously discussed, the label 30a enhances the visibility of the level of the photocurable material 14a in the vial 12a when the user is viewing the photocurable material 14a through the second portion 34a of label 30a, or through the gap between end portions of the label 30a. Advantageously, since the first section 32a also hinders transmission of actinic radiation, there is less likelihood than an undue amount of actinic radiation will reach the photocurable material 14a.

Figure 5:
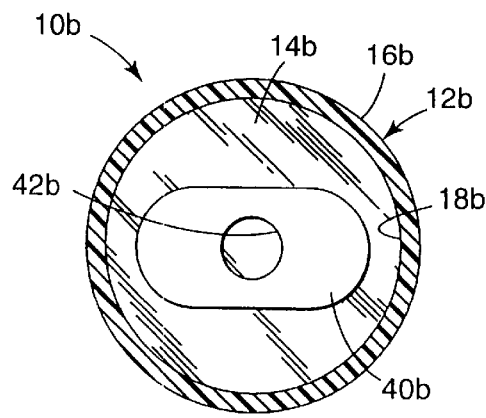
FIG. 5 is a horizontal sectional view taken along line 5—5 of FIG. 4.

Another embodiment of the invention is shown in FIGS. 4 and 5, wherein a packaged composition 10b includes a vial 12b and a photocurable material 14b. Both the vial 12b and the photocurable material 14b are preferably identical to the vial 12 and photocurable material 14 previously described, except for the differences set out below.

The vial 12b includes a float or element 40b that is received in the chamber 18b. The element 40b has a density less than the density of the photocurable material 14b, and as a result floats in the photocurable material 14b. The element 40b is visible through the side wall 16b that transmits light in a portion of the visible light spectrum, and thereby enhances the user's ability to determine the level or amount of photocurable material 14b in the chamber 18b.

Prefqrably, the element 40b has dimensions along two axes that are smaller than the dimensions of the outlet 26b so that the element 40b can be inserted into the chamber 18b through the outlet 26b after the vial 12b is manufactured. As an example, if the chamber 18b of the vial 12b has an internal diameter of 0.64 inches (1.6 cm), the element 40b may have overall dimensions of 0.25×0.50 inches (6.4×13 mm) and a thickness of 0.06 inches (1.5 mm). As illustrated in FIG. 5, the element 40b preferably has an overall generally oval-shaped configuration in plan view.

Preferably, the element 40b has a thickness in the approximating range of 0.01–0.06 inches (0.25–1.5 mm). The flat shape and relatively small thickness of the element 40b helps the element return to a horizontal orientation after the vial 12 has been inverted and then returned to the upright vertical orientation as depicted in the Figures. Moreover, the flat shape of element 40b tends to cast a more distinct shadow than a float having, for example, a spherical shape, and as a result is relatively easy to see through the side wall 16b. Further, the element 40b may have a central hole 42b. The hole 42b improves fluid flow of the photocurable material 14b to the outlet 26b when the vial 12b is inverted during a dispensing operation. The element 40b is made of a material that is inert to the photocurable material 14b. A suitable material for element 40b that is inert to many photocurable materials is polyethylene. The element 40b could be a liquid, a semi-liquid (gel or paste) or a solid material that is either hollow or not hollow, including materials which are foamed.

Figure 6:
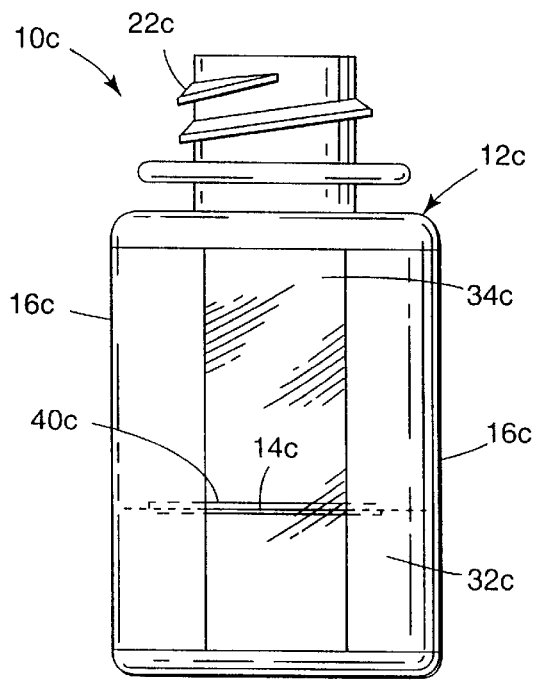
FIG. 6 is a view somewhat similar to FIG. 5 except in accordance with still another embodiment of the present invention.

Another embodiment of the invention is depicted in FIG. 6, wherein a packaged composition 10c includes a vial 12c and a photocurable material 14c, the latter of which is identical to the photocurable material 14 described previously.

The vial 12c has a generally oval-shaped overall configuration in plan view. A threaded neck portion 22c of the vial 12c is identical to the neck portion 22, and may receive a cap of the type previously described.

The vial 12c has an upright side wall 16c which includes a first section 32c that is preferably covered or at least substantially covered with a coating. Preferably, the coating is opaque or at least substantially opaque to the passage of light in the visible spectrum as well as in the actinic spectrum. An example of a suitable coating is an ink that in applied by pad printing or screen printing technique and preceded by a flame treatment to insure good adhesion of the ink to the vial 12c.

The upright side wall 16c includes a second portion 34c which lacks or substantially lacks the coating that is applied to the first section 32c. As a consequence, the second section 36c transmits more light in the visible spectrum than the light transmitted to the first section 32c, but still blocks actinic radiation by virtue of the colorant added to the polymeric material of the vial.

Additionally, the vial 12c includes a float or element 40c that is received in the chamber. The element 40c is somewhat similar to the element 40b, but is longer in length in order to better match the shape of the chamber in plan view. The first section 32c, the second section 34c and the element 40 help the user determine the level of photocurable material 14c in the chamber.

Those skilled in the art may recognize that a variety of alternatives are possible to the presently preferred embodiments described in detail above. For example, the shape of the vial may have another configuration, such as a configuration similar to squeezable tubes or squeezable containers of other configurations, and could be made of polymeric materials and colorants different from those materials and colorants previously set forth. Furthermore, the outlet could be open or covered with a sponge, brush, swab or other type of applicator. Accordingly, the scope of the invention should not be deemed limited by the specific descriptions mentioned above, but only by a fair reading of the claims that follow along with their equivalents.

What is claimed is:

1. A packaged composition comprising: a vial formed by a bottom wall and an elastic side wall circumscribing said bottom wall to define a chamber, said side wall having an upper section shaped to form an outlet in open communication with said chamber, said bottom and side walls being formed of a polymeric material having a colorant added thereto for substantially attenuating actinic radiation, said side wall having at least one upright portion capable of transmitting light having wavelengths greater than 500 nanometers, said side wall having a substantially uniform wall thickness; and a photocurable material disposed in said chamber and being cured responsive to exposure of actinic radiation, said photocurable material being dispensed through said outlet responsive to portions of said side wall being displaced from an initial position to a position closer together, subsequently said displaced portions of said side wall substantially returning to said initial position.

2. The packaged composition as recited in claim 1 where said substantially uniform wall thickness is within an approximating range of 0.015–0.025 inches.

3. The packaged composition as recited in claim 1 where said polymeric material has a flexural modulus less than approximately 200,000 kg/cm$^2$.

4. The packaged composition as recited in claim 1 where said polymeric material has a flexural modulus less than approximately 20,000 kg/cm$^2$.

5. The packaged composition as recited in claim 1 where said photocurable material has either an absolute viscosity less than 100 centipoise or a kinematic viscosity less than 1200 centistokes.

6. The packaged composition as recited in claim 1 where said side wall transmits less than 1.0% actinic radiation.

7. The packaged composition as recited in claim 1 where said side wall transmits less than 0.5% actinic radiation.

8. The packaged composition as recited in claim 1 further comprising a label secured to an external surface of a first portion of said side wall and extending from a position adjacent said bottom wall to a position adjacent said upper section thereof for enhancing visibility of a level of said photocurable material through a second portion of said side wall.

9. The packaged composition as recited in claim 1 where said colorant has a color in the orange portion of the visible light spectrum.

10. The packaged composition as recited in claim 9 where said colorant is added to said polymeric material to provide a colorant concentration of approximately 1%.

* * * * *

UNITED STATES PATENT AND TRADEMARK OFFICE
CERTIFICATE OF CORRECTION

PATENT NO.    : 6,179,125 B1
DATED         : January 30, 2001
INVENTOR(S)   : Kvitrud, James R.

It is certified that error appears in the above-identified patent and that said Letters Patent is hereby corrected as shown below:

Column 2,
Line 11, delete "Summury" and insert in place thereof -- Summary --.

Column 3,
Line 5, delete "." after -- initial --.
Line 64, delete "havp" and insert in place thereof -- have --.

Column 5,
Line 19, delete "470n." and insert in place thereof -- 470 nm. --.

Column 7,
Line 49, delete "Prefqrably" and insert in place thereof -- Preferably --.

Signed and Sealed this

Twenty-ninth Day of October, 2002

*Attest:*

JAMES E. ROGAN
*Director of the United States Patent and Trademark Office*

*Attesting Officer*